US00PP12135P2

(12) United States Plant Patent
Heims

(10) Patent No.: US PP12,135 P2
(45) Date of Patent: Oct. 9, 2001

(54) PULMONARIA PLANT NAMED 'SILVER STREAMERS'

(75) Inventor: Dan M. Heims, Portland, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 09/324,625

(22) Filed: Jun. 2, 1999

(51) Int. Cl.[7] ..... A01H 5/00
(52) U.S. Cl. ..... Plt./263
(58) Field of Search ..... Plt./263, 373

*Primary Examiner*—Bruce R. Campell
*Assistant Examiner*—Michelle Kizilkaya
(74) *Attorney, Agent, or Firm*—Klarquist Sparkman Campbell Leigh & Whinston LLP

(57) ABSTRACT

A new and distinct hybrid of Pulmonaria, characterized by its unique foliage with an intensely ruffled margin and a highly silvered upper leaf surface.

1 Drawing Sheet

The present invention relates to a new and distinct hybrid of Pulmonaria, which originated as a cross between Pulmonaria 'Excalibur' U.S. Plant Pat. No. 8,958 (pollen parent) and Pulmonaria 'Berries and Cream' U.S. Plant Pat. No. 10,597 (seed parent), both of hybrid origin, in the family Boraginaceae. Both parents originated in Canby, Oreg. As the instant and parent plants are of interspecific hybrid origins, no species designations are assigned.

This new Pulmonaria is a result of a controlled cross of the aforementioned plants in Canby, Oreg. This hybrid was selected from a large number of seedlings. Seed and pollen parent plants were retained to observe habit and to compare with the present invention. The new variety has been reproduced only by asexual propagation (division and tissue culture). Each of the progeny exhibits identical characteristics to the original plant and is unlike any Pulmonaria offered by any American nursery or in any book, known to the inventor, as evidenced by the following characteristics:

1. Strongly undulated leaf edges; and
2. Entirely silvered upper leaf surface with a fine edge of green highlighting the undulations.

Asexual propagation by division and tissue culture done in Tigard and Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE PHOTOGRAPH

The FIGURE shows distinctive foliage of Pulmonaria 'Silver Streamers'.

DETAILED PLANT DESCRIPTION

The following is a detailed description of the new Pulmonaria hybrid based on observations of two-year-old, field-grown specimens in Canby, Oreg. The color descriptions are all based on The Royal Horticultural Society Colour Guide.

Plant:

*Form.*—Herbaceous perennial, evergreen in USDA hardiness zones 6 to 9, dies back to the ground in USDA hardiness zones 4 and 5.

*Arrangement.*—Rosette.
*Habit.*—Clumping.
*Height and width.*—27 cm height by 28 cm width for one year's growth from a 3 cm plug.

Foliage:

*Type.*—Simple.
*Shape.*—Ovate to linear-lanceolate.
*Length.*—25 cm.
*Width.*—8 cm.
*Petiole length.*—8 cm.
*Margins.*—Ciliate, entire, undulate. Undulation is very tight as compared to other Pulmonaria. Undulations "ripple" 1 "wave" over the distance of 1 cm along the margin.
*Apex.*—Apiculate.
*Base.*—Acute.
*Pubescence.*—Uniform bristle-like pubescence, both upper and lower leaf surfaces.
*Venation.*—Reticulate-pinnate.
*Color.*—Upper surface — RHS Greyed Green Group 196C. Margins — RHS Green Group 137B. Lower surface — RHS Green Group 138B. Petiole base — RHS Greyed Purple Group 183D.

Flower:

*Description.*—Blooms in bracteated, forked, terminal cymes, with 12–15 flowers per cyme and 10–22 cymes per two-year-old plant.
*Peduncles.*—15–20 cm. long.
*Flower type.*—Complete, corolla is salverform; a cylindric tube with five obtuse lobes.
*Size.*—1.25–1.5 cm. wide and 2.0 cm. long.
*Petal.*—Lobe size: 0.6 cm. long and 0.7 cm. wide. Texture: smooth, undulate. Color: ranges from RHS 66 A Red-Purple Group to RHS 66D Red-Purple Group. Same color inside and out of the flower. Throat color: RHS 66 A Red-Purple Group.
*Calyx.*—Color: RHS 183D Greyed Purple Group. Shape: tubular-campanulate, 5 toothed. Size:1.5 cm. long and 0.4 cm. wide. Texture: calyx has a uniform bristle-like pubescence.
*Stamens.*—5, included in calyx tube with white pollen, as typical of the genus.
*Pistil.*—Not exerted (thrum-type).
*Placentation.*—One-chambered, basal.
*Fruit.*—4 smooth nutlets, each one seeded.

*Fragrance.*—None.

*Lastingness of bloom.*—5 to 7 days.

*Bloom period.*—Second week of March to last week in April in Canby, Ore.

Disease: None observed on plants grown under commercial condition in Canby, Oreg.

COMPARISON WITH PARENT PLANTS

This Pulmonaria hybrid has characteristics which make it unique from its parents, Pulmonaria 'Excalibur', U.S. Plant Pat. No. 8,958 (pollen parent), and Pulmonaria 'Berries and Cream' U.S. Plant Pat. No. 10,597 (seed parent). The flowers are not distinctive on Pulmonaria 'Silver Streamers'. Pulmonaria 'Berries and Cream', U.S. Plant Pat. No. 10,597, has spotting, whereas Pulmonaria 'Silver Streamers' is entirely silvered with a very narrow green margin. Pulmonaria 'Excalibur', U.S. Plant Pat. No. 8,958, has a wide, dark green edge along the margin and great contrast between the silvering and the dark edge , whereas Pulmonaria 'Silver Streamers' appears almost completely silver with a very thin green edge. The extreme undulation of Pulmonaria 'Silver Streamers' differs from the undulations of both parents. No other Pulmonaria, known to the inventor, resembles Pulmonaria 'Silver Streamers'.

I claim:

1. A new and distinct hybrid of Pulmonaria plant substantially as shown and described, characterized by its unique foliage with an intensely ruffled margin and a highly silvered upper leaf surface.

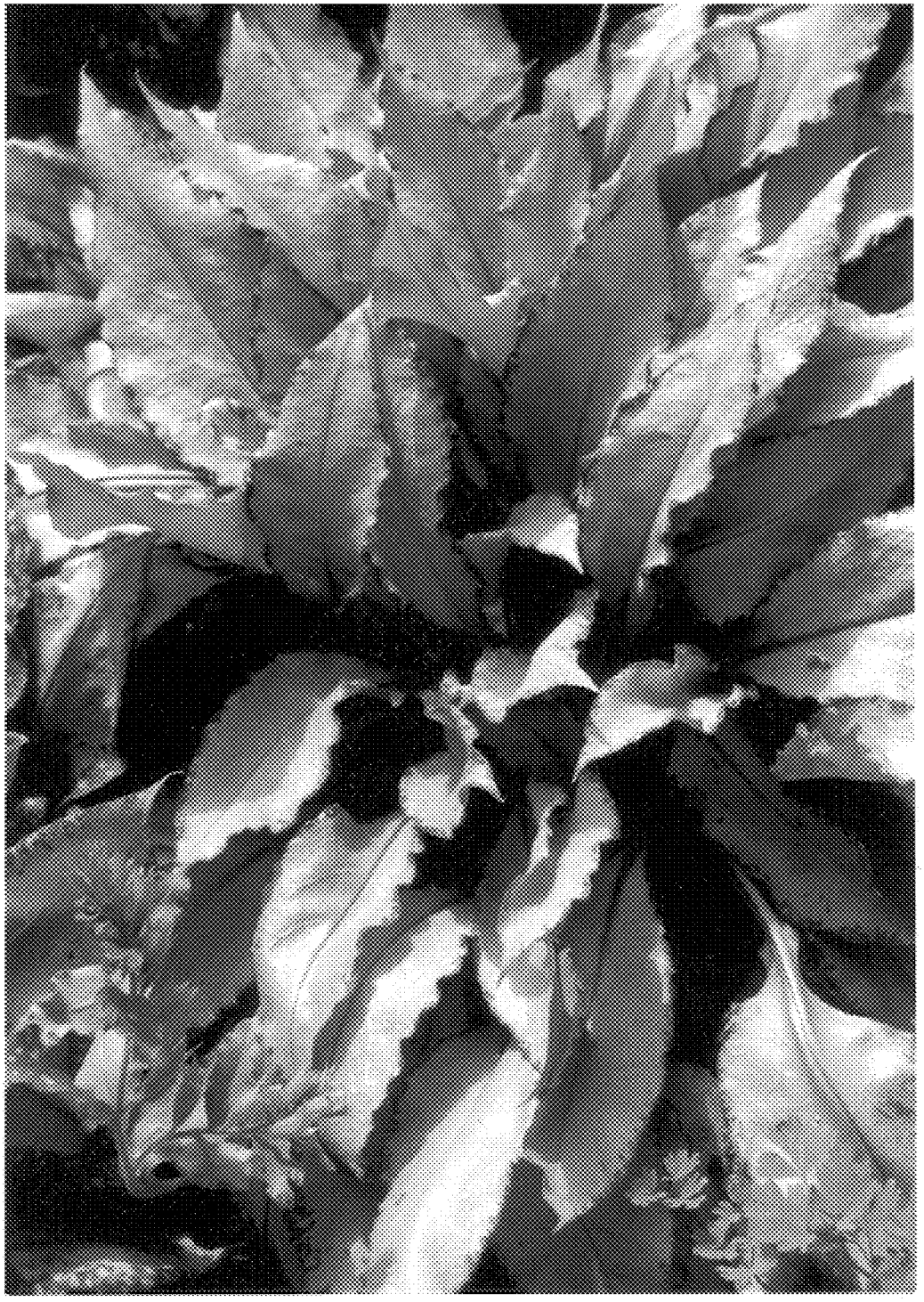

* * * * *